United States Patent
Kang et al.

(10) Patent No.: US 11,753,765 B2
(45) Date of Patent: Sep. 12, 2023

(54) BIOMIMETIC SELF-ADAPTABLE SYSTEMS

(71) Applicant: The Johns Hopkins University, Baltimore, MD (US)

(72) Inventors: Sung Hoon Kang, Lutherville-Timonium, MD (US); Santiago Orrego, Philadelphia, PA (US)

(73) Assignee: The Johns Hopkins University, Baltimore, MD (US)

( * ) Notice: Subject to any disclaimer, the term of this patent is extended or adjusted under 35 U.S.C. 154(b) by 493 days.

(21) Appl. No.: 16/645,317

(22) PCT Filed: Sep. 10, 2018

(86) PCT No.: PCT/US2018/050237
§ 371 (c)(1),
(2) Date: Mar. 6, 2020

(87) PCT Pub. No.: WO2019/051395
PCT Pub. Date: Mar. 14, 2019

(65) Prior Publication Data
US 2021/0040678 A1 Feb. 11, 2021

Related U.S. Application Data

(60) Provisional application No. 62/555,983, filed on Sep. 8, 2017.

(51) Int. Cl.
| | | |
|---|---|---|
| D06M 10/04 | (2006.01) | |
| A61L 27/44 | (2006.01) | |
| A61L 27/50 | (2006.01) | |
| B32B 33/00 | (2006.01) | |
| D01F 1/10 | (2006.01) | |
| D01F 6/12 | (2006.01) | |

(Continued)

(52) U.S. Cl.
CPC ........... D06M 10/04 (2013.01); A61L 27/44 (2013.01); A61L 27/50 (2013.01); B32B 33/00 (2013.01); D01F 1/10 (2013.01); D01F 6/12 (2013.01); D06M 16/00 (2013.01); F16F 15/007 (2013.01); D10B 2401/18 (2013.01)

(58) Field of Classification Search
None
See application file for complete search history.

(56) References Cited

U.S. PATENT DOCUMENTS 4,557,880 A * 12/1985 Pantelis .................. H01L 41/45
427/100
5,522,879 A * 6/1996 Scopelianos ............ A61L 27/16
602/41

(Continued)

FOREIGN PATENT DOCUMENTS

WO    WO2014161920    * 10/2014

OTHER PUBLICATIONS

International Search Report and Written Opinion for PCT/US2018/050237. dated Mar. 25, 2019. 9 pages.

(Continued)

*Primary Examiner* — Shawn McKinnon
(74) *Attorney, Agent, or Firm* — CASIMIR JONES, SC; Brian F. Bradley

(57) ABSTRACT

Self-adaptive systems, uses of the systems, and methods for adapting one or more properties of a material are disclosed.

16 Claims, 7 Drawing Sheets

(51) Int. Cl.
*D06M 16/00* (2006.01)
*F16F 15/00* (2006.01)

(56) References Cited

U.S. PATENT DOCUMENTS

| | | | |
|---|---|---|---|
| 5,532,217 | A | 7/1996 | Silver et al. |
| 6,767,928 | B1 | 7/2004 | Murphy et al. |
| 8,541,031 | B2 | 9/2013 | Mount et al. |
| 9,206,233 | B2 | 12/2015 | Rosi et al. |
| 9,371,451 | B2 | 6/2016 | Mount et al. |
| 2007/0087959 | A1 | 4/2007 | Sfeir et al. |
| 2008/0058445 | A1 | 3/2008 | Dry |
| 2009/0136594 | A1 | 5/2009 | Mcleroy et al. |
| 2013/0226105 | A1 | 8/2013 | Hyde et al. |
| 2014/0342192 | A1 | 11/2014 | Wang et al. |
| 2016/0050916 | A1 | 2/2016 | Bellido-Gonzalez et al. |

OTHER PUBLICATIONS

Alves et al., Designing biomaterials based on biomineralization of bone. Journal of Materials Chemistry, 2010. 20(15), 2911-2921.

Gupta et al., Recent advances on surface engineering of magnetic iron oxide nanoparticles and their biomedical applications. Nanomedicine (Lond). Feb. 2007;2(1):23-39.

Kepa et al., In vitro mineralization of functional polymers. Biosurface and Biotribology, 2015. 1(3), 214-227.

Lin et al., Advances in synthesis of calcium phosphate crystals with controlled size and shape. Acta Biomater. Oct. 2014;10(10):4071-102.

Mann. Biomineralization: principles and concepts in bioinorganic materials chemistry (vol. 5). Oxford University Press on Demand. 2001. TOC only. 9 pages.

Meldrum et al., Controlling mineral morphologies and structures in biological and synthetic systems. Chem Rev. Nov. 2008;108(11):4332-432.

Soroushian et al., Piezo-driven shelf-healing by electrochemical phenomena. Journal of Intelligent Material Systems and Structures. 2012. 24(4) 441-453.

Stitz et al., Piezoelectric Templates—New Views on Biomineralization and Biomimetics. Sci Rep. May 23, 2016;6:26518. 7 pages.

Xu et al., Biomimetic mineralization. J. Mater. Chem. 2007. 17(5), 415-449.

Zhu et al., The effect of surface charge on hydroxyapatite nucleation. Biomaterials. Aug. 2004;25(17):3915-21.

\* cited by examiner

BIOMIMETIC SELF-ADAPTABLE SYSTEMS

CROSS-REFERENCE TO RELATED APPLICATION

This application claims the benefit of U.S. Provisional Application No. 62/555,983, filed Sep. 8, 2017, which is incorporated herein by reference in its entirety.

BACKGROUND

Current synthetic composite materials for engineering applications have fixed properties. Subjecting these materials to mechanical stresses (e.g., cyclic loading) could give rise to crack initiation, propagation and eventual catastrophic failure, even at load amplitudes lower than their yield strength. Accordingly, there is a need to design new composite materials with properties that can respond to their external environment, as well as material that can self-heal. By having these properties, composite materials may offer several benefits, including delaying material damage and adaptable mass optimization. These attributes may present new avenues and opportunities for material design in a variety of applications, such as biomedical, automotive, and aerospace.

SUMMARY

In one aspect, the present disclosure provides self-adaptive material systems including a substrate comprising a piezoelectric material, the substrate having a first surface configured to generate a first charge upon application of a mechanical stress to the substrate; and a liquid comprising a plurality of ions in contact with the first surface, wherein at least one ion of the plurality of ions electrostatically couples to the first surface of the substrate in response to the generation of the first charge on the first surface.

In another aspect, the present disclosure provides methods of adapting one or more effective properties of a material comprising contacting a substrate comprising a piezoelectric material with a liquid comprising a plurality of ions; and applying a mechanical stress to the substrate to provide a material having one or more adapted properties.

In other aspects, the present disclosure provides uses of the self-adaptive systems.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
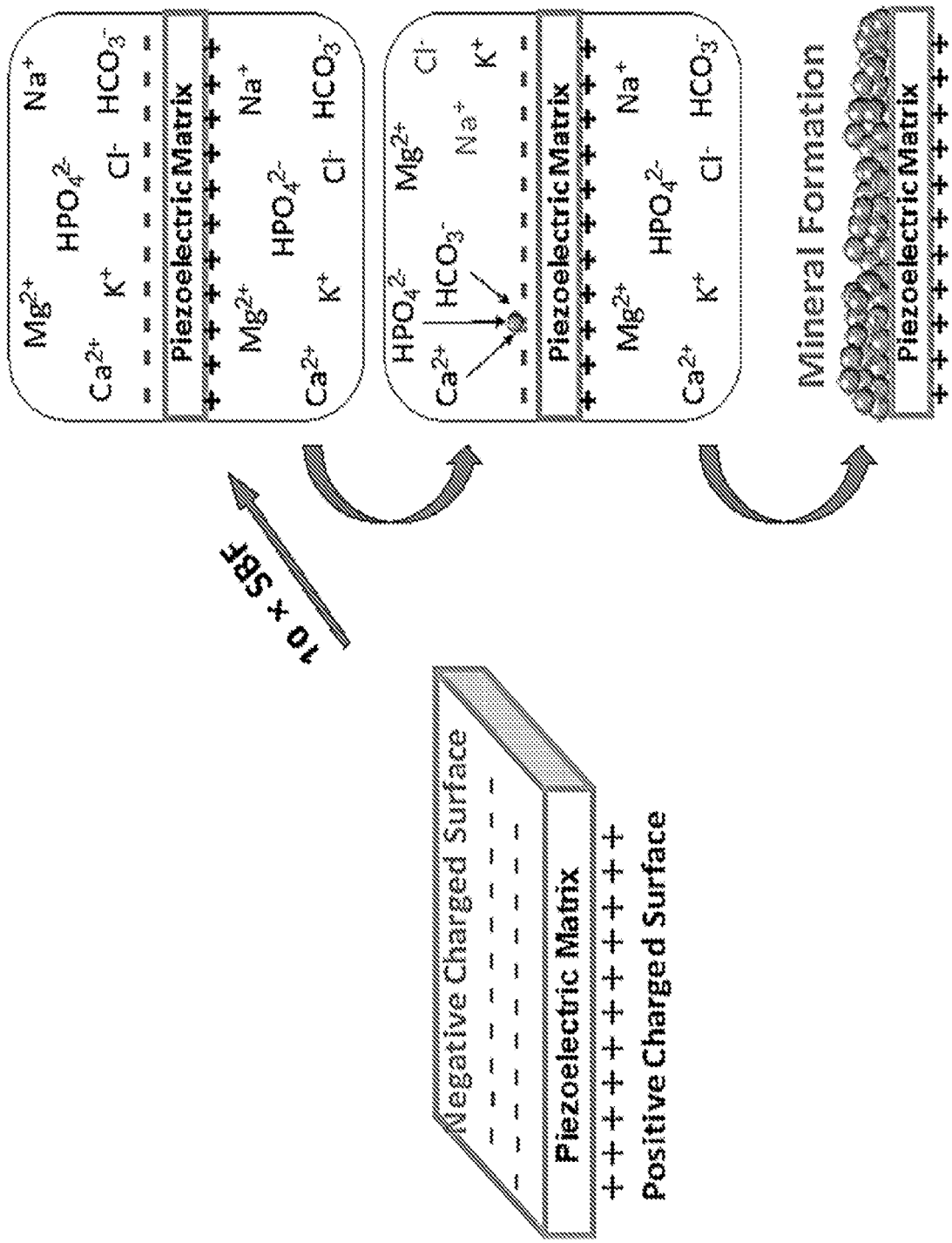
Figure 2A:
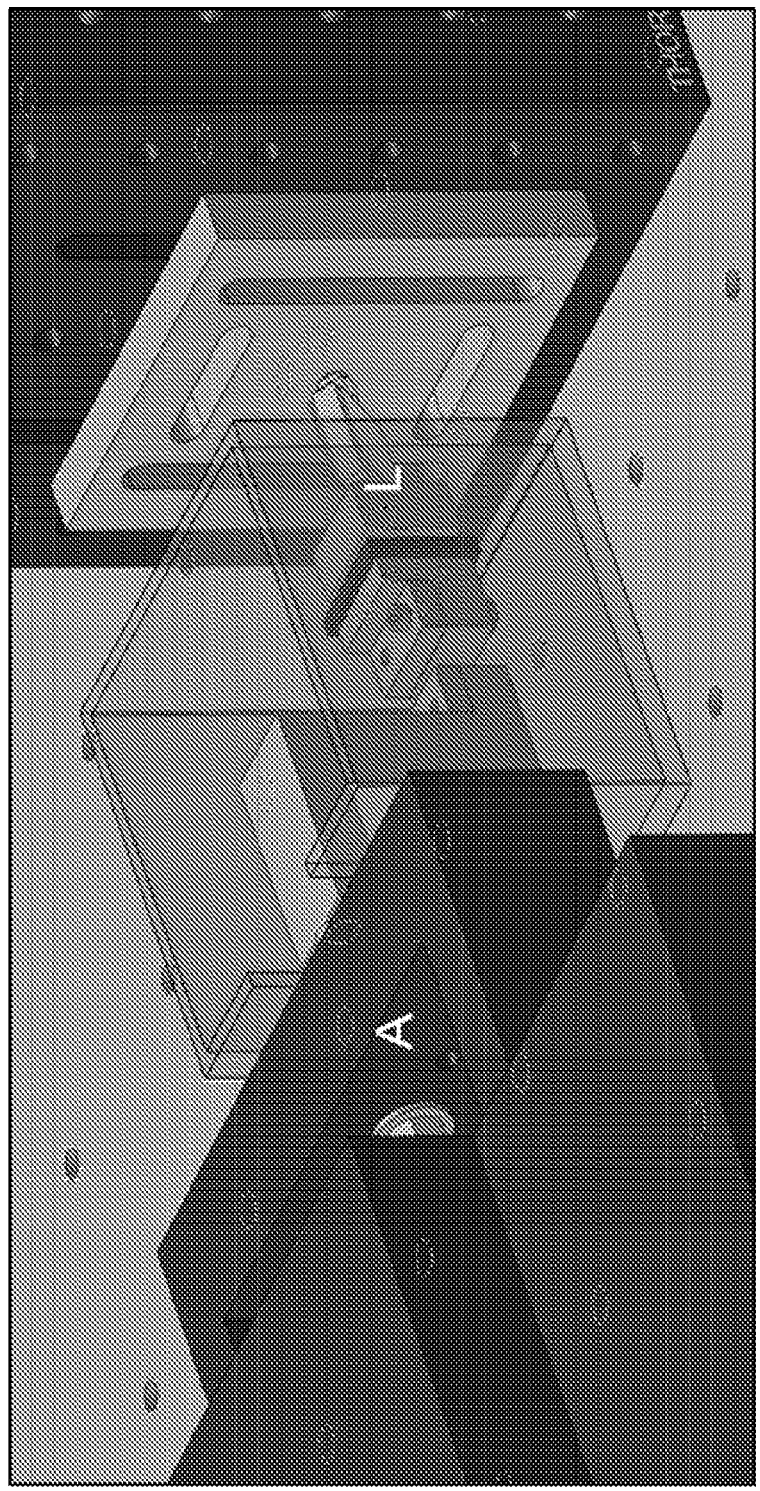
Figure 2B:
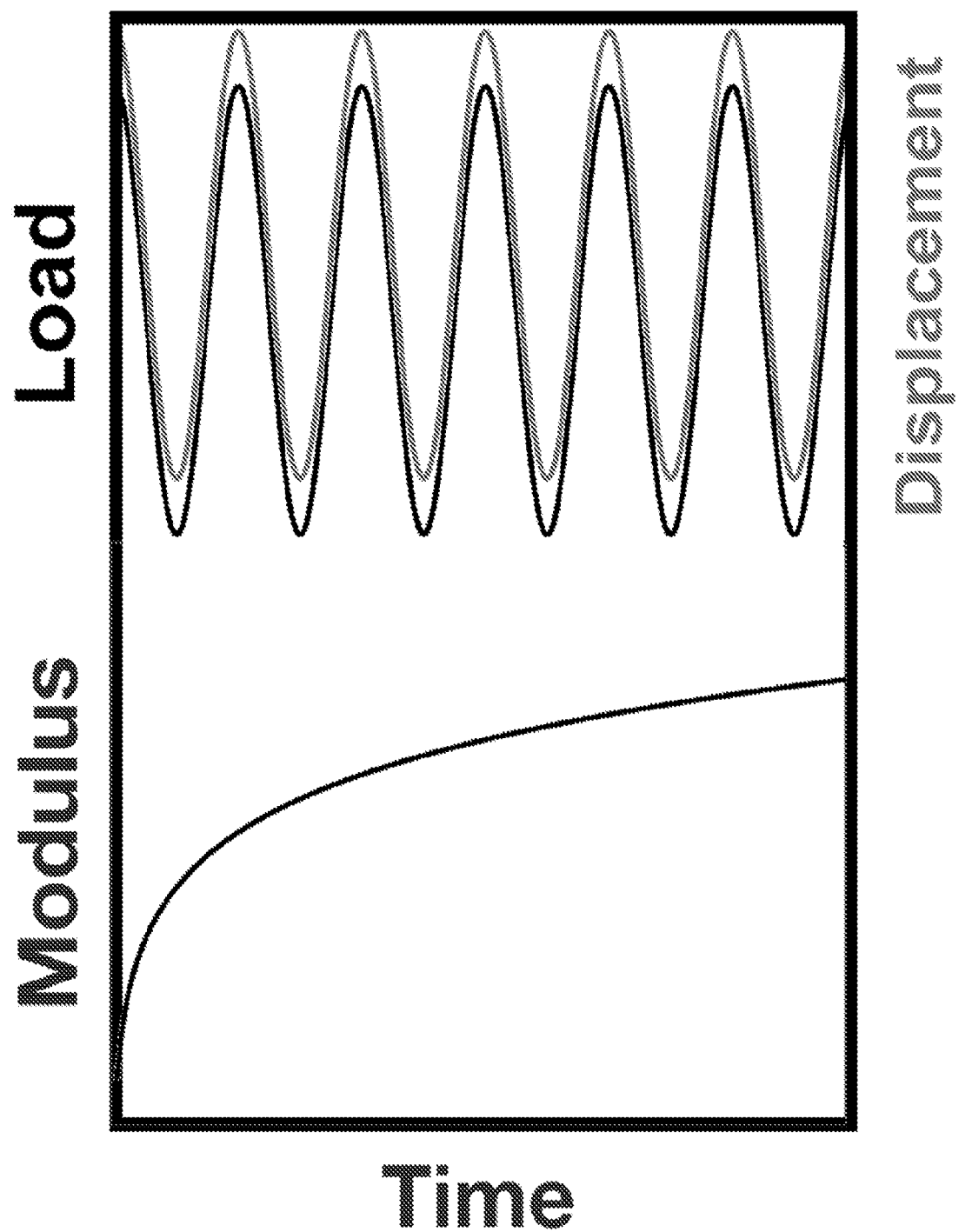
Figure 2C:
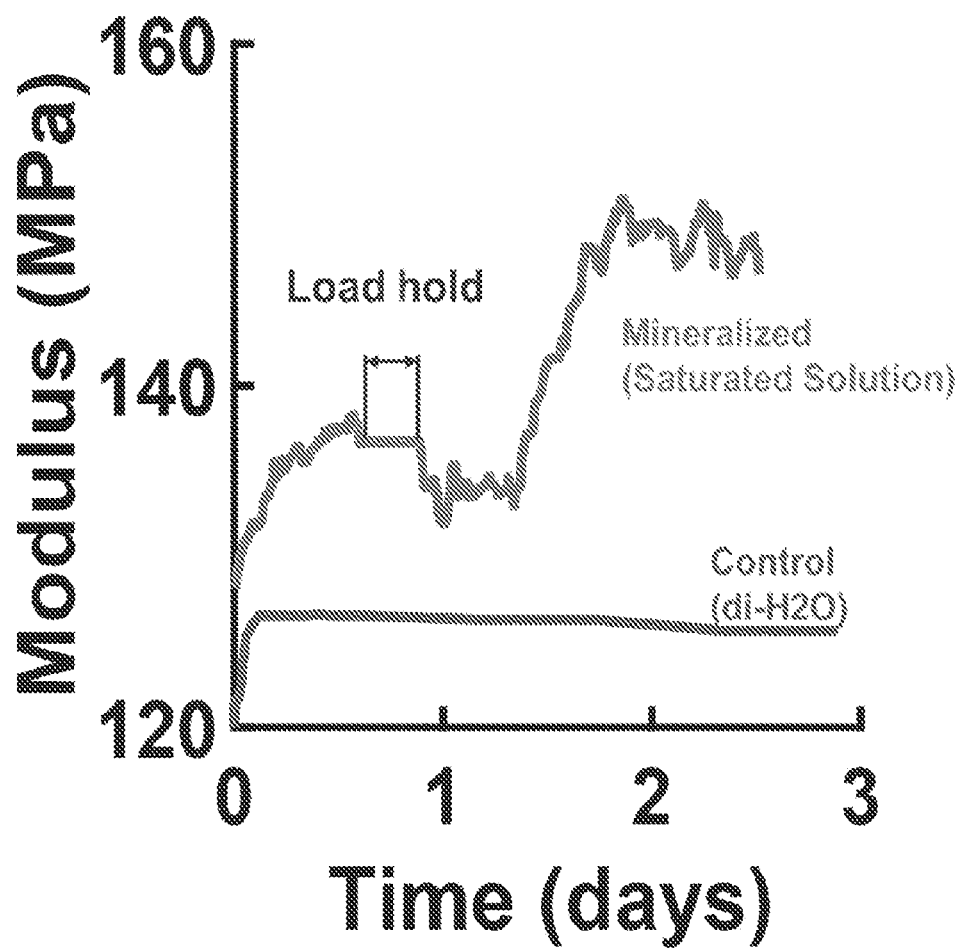
Figure 2D:
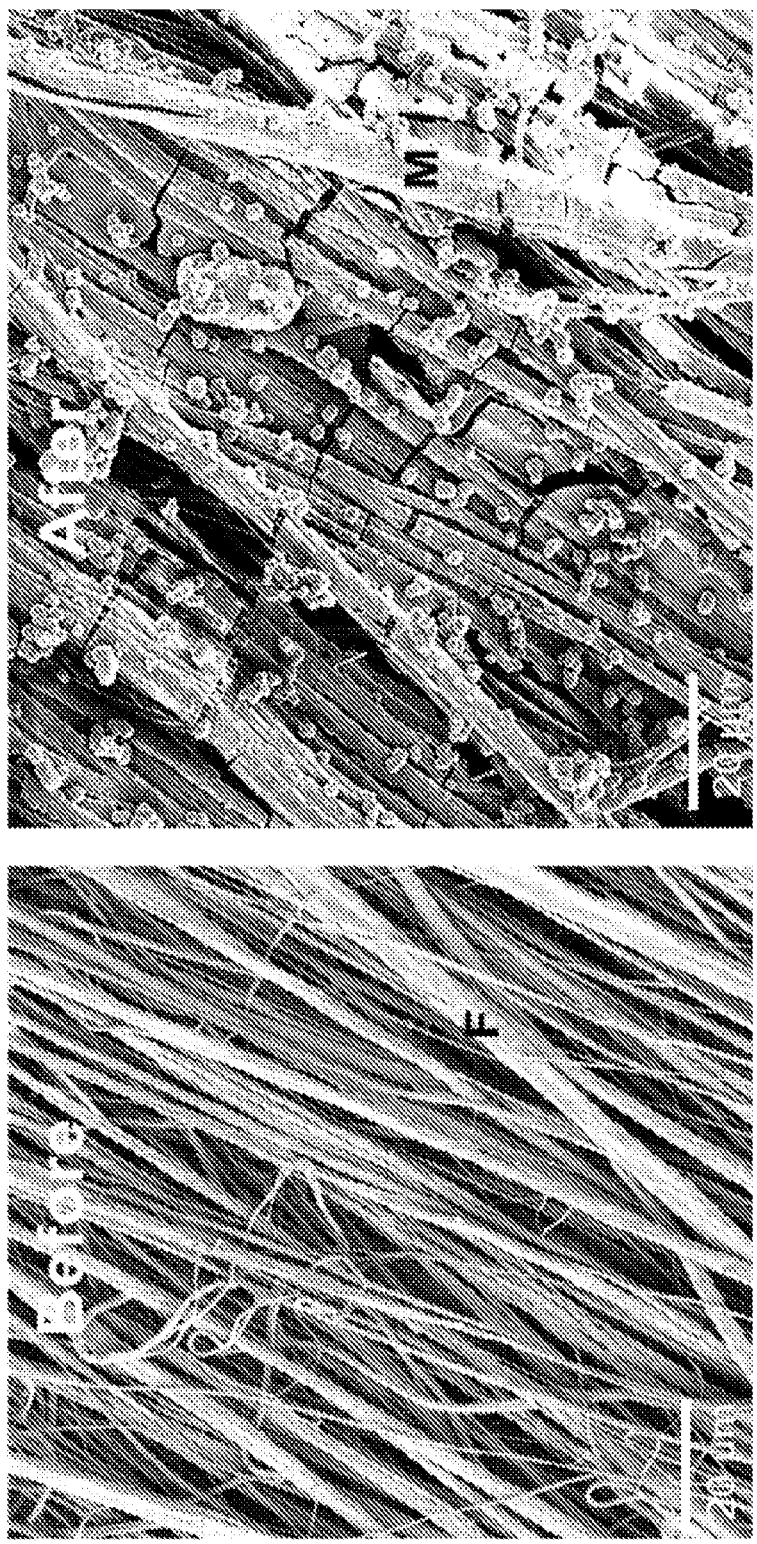
Figure 3A:
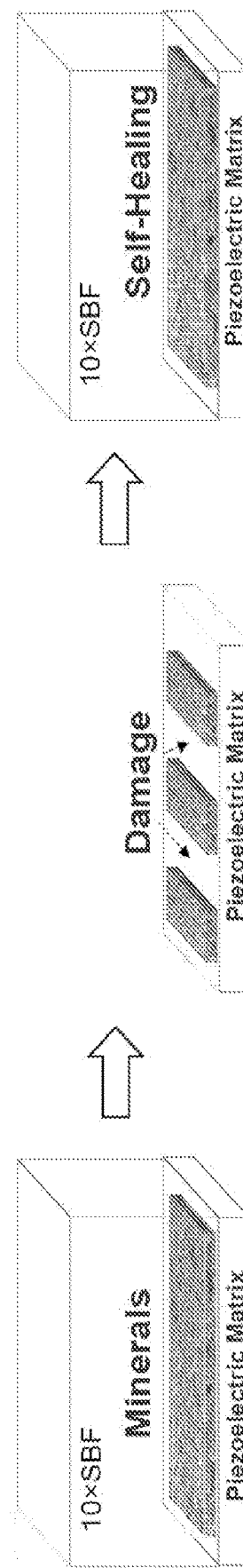
Figure 3B:
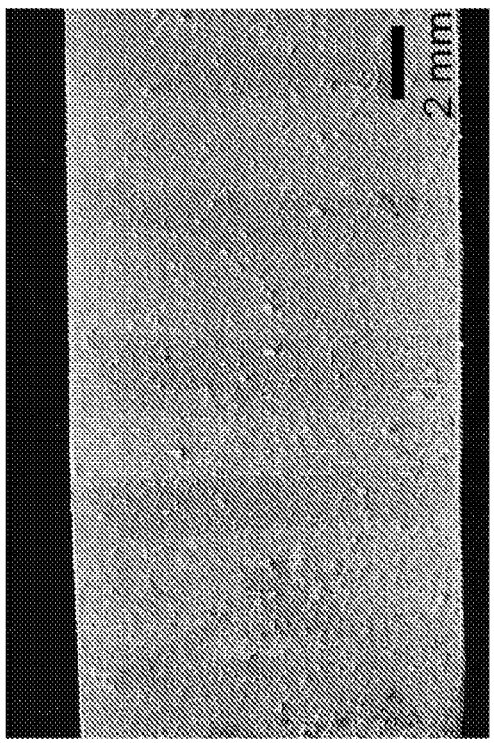
Figure 3B:
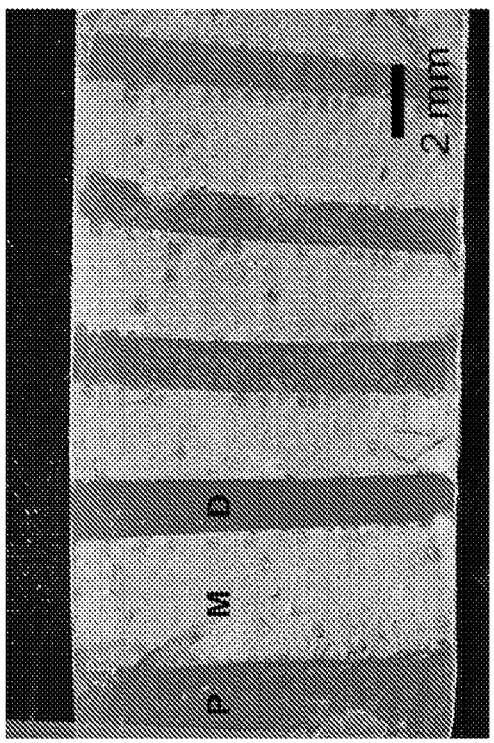

Having thus described the presently disclosed subject matter in general terms, reference will now be made to the accompanying Figures, which are not necessarily drawn to scale, and wherein:

FIG. 1 shows a schematic of a proposed mechanism that may be employed to self-stiffen and/or self-repair an exemplary self-adaptive system. SBF: Simulated body fluid;

FIG. 2A, FIG. 2B, FIG. 2C and FIG. 2D show mechanical self-adaptation of an exemplary self-adaptive system upon cycle loading. FIG. 2A shows a CAD drawing of the experimental setup used to subject the piezoelectric matrix to cyclic loading while being submerged in an aqueous solution. The actuator (A) can be programmed to cyclically load the sample (S) using an arbitrary wave shape. The load cell (L) can record the amount of force applied to the sample. FIG. 2B shows schematics for the load profile applied to the piezoelectric matrix and the resultant self-stiffening of an exemplary self-adaptive system. FIG. 2C shows the self-adaptable stiffness of a PVDF-based material system immersed in a SBF aqueous solution. The control response corresponds to the same PVDF-based material system immersed in a control solution, e.g., water. FIG. 2D shows SEM images of an exemplary piezoelectric matrix before and after the self-stiffening experiments. F: aligned fibers (F): and M: mineralized fibers (M); and FIG. 3A and FIG. 3B show seal-healing capabilities of an exemplary self-adaptive system. FIG. 3A shows a schematic of the self-healing process. FIG. 3B shows the coated piezoelectric scaffold (P) with minerals (M). Damage scratches were introduced as band stripes (image on the left). After re-immersing the sample for 7 days in SBF, the damaged regions were repopulated with minerals via piezoelectric mineralization (image on the right), demonstrating the self-healing capability.

DETAILED DESCRIPTION

The presently disclosed subject matter now will be described more fully hereinafter with reference to the accompanying Figures, in which some, but not all embodiments of the presently disclosed subject matter are shown. The presently disclosed subject matter may be embodied in many different forms and should not be construed as limited to the embodiments set forth herein: rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Self-Adaptive Systems

In one embodiment, disclosed are self-adaptive systems (which also are referred to as self-healing systems and self-stiffening systems herein). The self-adaptive systems include a substrate comprising a piezoelectric material. The substrate has a first surface configured to generate a first charge upon application of a mechanical stress to the substrate. In addition, the self-adaptive systems include a liquid comprising a plurality of ions, wherein at least one ion of the plurality of ions electrostatically couples to the first surface of the substrate in response to the generation of the first charge on the first surface.

It has been found that the disclosed self-adaptation and self-healing systems can respond to external stimuli, such as external mechanical loading and damage. The adaptation of properties is based on the controlled deposition of a new phase (e.g., ions and/or minerals) along a matrix which is externally stimulated via mechanical stress or exposure of charges on the first surface after damage of a mineral layer. The disclosed self-adaptive systems include an electroactive matrix, or piezoelectric material, to generate electrical charges in response to external loading.

Piezoelectricity is the ability of certain materials to convert mechanical energy into electrical energy or vice versa. The electrical charges can drive the deposition of the new phase (such as ions and/or minerals) from liquids into site-specific regions within the system, which can instill self-stiffening and self-healing features. Thus, by controlling the addition of ions and/or minerals in association with external forces it may be possible to modulate the material properties. In addition, the disclosed self-adaptive systems may self-stiffen and/or self-heal without the aid of biological cells (e.g., a cell derived from a biological organism). For example, in some embodiments, the self-adaptive system is free of biological cells.

FIG. 1 provides a schematic of a hypothesized mechanism of an exemplary self-adaptive system that can self-stiffen and/or self-repair. In this schematic, the piezoelectric-based substrate is immersed in an ionic solution including simulated body fluid (SBF). External cyclic loading can stimulate the substrate, thereby generating an electrical charge. Minerals, e.g., calcium phosphates and/or calcium carbonates, may nucleate, grow and bind into the negatively charged surface on the substrate. Mineralization may then occur via electrostatic interaction between the positive $Ca^{2+}$ ions present in SBF and the negatively charged surface activated via external loading or damage of a mineral layer.

A. Substrate

The substrate may have more than a first surface, and may have at least two surfaces, the two surfaces being a first surface and a second surface. For example, in addition to the first surface, the substrate may have a second surface configured to generate a second charge. Depending on the location of the surface on the substrate, the charge may be positive or negative. In some embodiments, the first surface and the second surface are on opposing sides of the substrate and have the generation of opposite charges upon a mechanical stress. In some embodiments, the first surface is configured to generate a first charge by including the piezoelectric material as at least a portion of the first surface. In some embodiments, the piezoelectric material makes up the entirety of the first surface of the substrate. In addition, the substrate may be shaped in any manner that is suitable for its intended application.

As mentioned above, the substrate includes a piezoelectric material. Examples of piezoelectric materials include, but are not limited to, polyvinylidene fluoride (PVDF), poly(vinylidene fluoride trifluoroethylene) (PVDF-TrFE), lead zirconate titanate ($Pb[Zr_xTi_{1-x}]O_3$ $0<x<1$), barium titanate ($BaTiO_3$), berlinite ($AlPO_4$), quartz ($SiO_2$), potassium sodium tartrate ($KNaC_4H_4O_6*4H_2O$), topaz $Al_2SiO_4(F,OH)_2$, gallium orthophosphate ($GaPO_4$), Langasite ($La_3Ga_5SiO_{14}$), lead titanate ($PbTiO_3$), potassium niobate ($KNbO_3$), lithium niobate ($LiNbO_3$), lithium tantalate ($LiTaO_3$), sodium tungstate ($Na_2WO_3$), $Ba_2NaNb_5O_5$, $Pb_2KNb_5O_5$, Poly(γ-benzyl α,L-glutamate) (PBLG), Poly-L-lactide (PLLA), sodium potassium niobate ((K,Na)$NbO_3$), bismuth ferrite ($BiFeO_3$), piezoelectric composites (e.g., mixtures of polymers, piezoelectric particles, and conductive fillers), collagen, and combinations thereof. The piezoelectric material may have a piezoelectricity coefficient of at least about 1 pC/N to about 2,000 pC/N. In some embodiments, the substrate consists essentially of a piezoelectric material. In some embodiments, the substrate is a piezoelectric material. In some embodiments, the piezoelectric material is PVDF.

In some embodiments, the piezoelectric material includes a plurality of fibers, such as fibers made from electrospinning techniques. The piezoelectric fibers may have varying diameters. For example, the plurality of fibers may have an average diameter of about 100 nm to about 100 micrometers. In principle, however, there is no limit to the diameter of the fibers for which the presently disclosed subject matter is applicable.

In some embodiments, the substrate and/or the piezoelectric material is not chemically modified. For example, in these embodiments, the substrate and/or the piezoelectric material do not have any of its surfaces chemically modified with functional groups, such as hydroxyl groups, carboxyl groups, phosphate groups, sulfonate groups, and phosphorylated groups. In other words, the disclosed substrates can rely on the electrical charge generation of the piezoelectric material, and not charge instilled on a surface by the inclusion of added, charged functional groups. One of ordinary skill in the art would appreciate that although added, charged functional groups are not necessary, they can be added if so desired.

B. Liquid

The liquid may be a solution, a suspension, or a supersaturated solution, and may be in direct contact with the substrate. The liquid may include any ion(s) that can electrostatically interact with a charge on the surface of the substrate. The plurality of ions in the liquid may precipitate out of the liquid in order to electrostatically interact with a charge on the surface of the substrate. Different ions can interact with different charges, and once an ion electrostatically couples with a charge, that bound ion can then interact with other charged ions in the liquid. For example, a negatively charged surface may interact with $Ca^{2+}$ ions, which in turn may interact with phosphates and/or carbonates in the liquid to provide and/or promote mineral growth on the surface of the substrate (e.g., calcium phosphate growth). Examples of ions include, but are not limited to, $Ca^{2+}$, $HPO_4^{-2}$, $HCO_3^-$, $CO_3^{-2}$, and $Cu^{2+}$, or combinations thereof. In some embodiments, the liquid is a supersaturated solution including $Ca^{2+}$, $HPO_4^{-2}$, and/or $HCO_3^-$.

The plurality of ions may be present at varying concentrations. For example, the plurality of ions may be present at a concentration of greater than about 1 mM.

In some embodiments, the liquid is a biological fluid. A "biological fluid" refers to any fluid originating from a biological organism. Exemplary biological fluids can include, but are not limited to, blood, serum, plasma, lymph fluid, bile fluid, urine, saliva, mucus, sputum, tears, cerebrospinal fluid (CSF), bronchioalveolar lavage, nasopharyngeal lavage, rectal lavage, vaginal lavage, colonic lavage, nasal lavage, throat lavage, synovial fluid, semen, ascites fluid, pus, maternal milk, ear fluid, sweat, and amniotic fluid. A biological fluid can be in its natural state or in a modified state by the addition of components such as reagents, or removal of one or more natural constituents (e.g., blood plasma). In some embodiments, the liquid is sea water.

II. Uses of the Self-Adaptive Systems

In other embodiments, disclosed are uses of the self-adaptive systems. The self-adaptive systems can be useful for a variety of different applications, including biomaterials, adsorbents, chemical engineering materials, catalysts and catalyst supports, and environmental sciences and mechanical reinforcements. In particular, the self-adaptive systems may be used in the aerospace and automotive industries due to their need for strong (for load bearing applications) and lightweight (to minimize transportation energy-fuel) materials. Because these two qualities are mutually exclusive, the disclosed self-adaptive systems may be able to bridge the gap between the two desired properties due to their ability to self-stiffen in response to external loading. The self-adaptable systems may become stronger in specific regions of maximum stress in response to external loading, thereby site-specifically redistributing the composite phases (minerals over piezoelectric material) and potentially optimizing the mass. Accordingly, the energy cost associated with transportation may be reduced via application of the self-adaptive systems.

In addition, the self-adaptive systems may be useful to mimic the mineralization processes found in bone and teeth. In particular, the self-adaptive systems may be useful in bone graft applications. The self-adaptive systems may provide improved production efficacy and customization of bone scaffolds via site-specific mineral deposition.

III. Methods of Adapting One of More Properties of a Material

In another aspect, disclosed are methods of adapting one or more properties of a material. Such properties include, but are not limited to, modulus, fatigue, strength, toughness, hardness (or wear resistance), density of the composite, permeability, electrical/thermal conductivity, heat capacity, thermal diffusivity, and the like. Further, the presently disclosed methods could affect chemical or biological properties of the material as there are changes of mineral build-up.

The method may include contacting a substrate comprising a piezoelectric material with a liquid comprising a plurality of ions. Generally, the description regarding the substrate and the liquid as described above can be applied to the disclosed methods. For the purposes of brevity, this description will not be repeated here.

The substrate and the liquid may be contacted for varying periods of time, such as for minutes, hours, days, weeks, or years. The substrate and the liquid may be contacted in different environments. For example, the substrate and the liquid may be contacted in an in vitro environment or in an in vivo environment. An example of an in vivo environment can be the substrate being used as part of a bone graft and the liquid being a native biological fluid.

The method may further include applying a mechanical stress to the substrate to provide a material having one or more adapted properties. The mechanical stress may be any type of stress sufficient to induce charge generation in the piezoelectric material. Examples of mechanical stress include, but are not limited to, cyclic stress, vibration, pressure, force, acceleration, strain, sound, quasistatic loading, periodic loading, impact, flow-induced stress, e.g., wave, wind, and the like, and combinations thereof.

The mechanical stress may be applied at varying forces. For example, the mechanical stress may be applied at a force of about 0 N to about 5 N. One of ordinary skill in the art would appreciate that any force could be used as long as the material does not fail. Further, lower forces could work for smaller diameter fibers.

The mechanical stress may be applied at varying frequency. For example, the mechanical stress may be applied at a frequency of about 0.5 Hz to about 10 Hz, such as about 0.75 Hz to about 4 Hz or about 1 Hz to about 3 Hz, or higher. The frequency ranges listed are particularly relevant to body motions.

The mechanical stress may be applied for varying amounts of time. For example, the mechanical stress may be applied for a period of time of about 1 second, 30 seconds, 1 minute, 5 minutes, 0.5 h to about 1 year, such as from about 0.5 h to about 6 months, about 1 h to about 1 month, or about 0.5 h to about 2 weeks.

The varying parameters for applying the mechanical stress as listed above can allow for site-specific deposition of ion(s) onto the surface of the substrate and/or piezoelectric material. In addition, by controlling the mechanical stress parameters, it may be possible to control the rate and amount of the ion(s) deposited onto the surface of the substrate and/or piezoelectric material. The rate of deposition of ion(s) onto the surface of the substrate and/or piezoelectric material should be faster than the potential dissolution of minerals within, for example, the SBF.

Following the application of the mechanical stress, the material having one or more adapted properties comprises the substrate, at least one ion of the plurality of ions, and at least one ion electrostatically coupled to a surface of the substrate. In addition, following applying the mechanical stress the material having one or more adapted properties may have an increase in modulus of at least 1.1× relative to the modulus of the substrate prior to applying the mechanical stress. In some embodiments, the material may have an increase in modulus of at least 1.2×, at least 1.3×, at least 1.4×, at least 1.5×, at least 1.6×, at least 1.7×, at least 1.8×, at least 1.9×, or at least 2×, or higher, relative to the modulus of the substrate prior to applying the mechanical stress.

IV. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments 5%, in some embodiments ±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Self-Stiffening of Composite Materials

This example demonstrates the experimental setup and the self-stiffening response of a self-adaptive system in response to external cyclic loading. FIG. 2(A) shows a CAD drawing of the experimental setup used to subject the piezoelectric matrix to cyclic loading while being submerged in SBF. The actuator (A) was programmed to cyclically load the sample (S) using a sine-wave shape. The load cell (L) recorded the amount of force applied to the sample. A displacement sensor measures the strain at the sample. The stiffness is calculated by dividing the force over the displacement, allowing the quantification of stiffness and self-adaptable properties. During cyclic loading the sample was constantly immersed in SBF held in the acrylic container. FIG. 2(B) shows schematics for the load profile applied to the piezoelectric matrix and the resultant self-stiffening (e.g., modulus increase with time) of the self-adaptive system. FIG. 2(C) shows a PVDF matrix and SBF in an aqueous environment. Cyclic loading was applied for 7 days at a frequency of 2 Hz. The increase of modulus in response to external loading is evident. The negative charges of the piezoelectric matrix (activated during loading) induces the precipitation, nucleation and growth of minerals along the matrix, thus, self-adapting the modulus. The addition of the new mineral phase on the substrate contributed to the self-stiffening and change in properties. FIG. 2(D) shows SEM images of a piezoelectric matrix before and after the self-stiffening experiments. For this experiment, electrospun PVDF scaffolds were utilized with aligned fibers (F). After subjecting the scaffold to cyclic loading, calcium phosphate minerals formed along the mineralized fibers (M) and contributed to the changes in modulus.

Example 2

Self-Healing of Composite Materials

This example demonstrates the seal-healing capabilities of a self-adaptive system. FIG. 3(A) shows a schematic of a proposed self-healing process. Initially, minerals were deposited onto the piezoelectric scaffold via electrostatic interactions between negatively charged surface and positive calcium ions from aqueous solution. Damage was applied by scratching the substrate. The substrate was re-immersed in the SBF solution and minerals were redeposited in the affected region covering damaged locations. FIG. 3(B) shows the coated piezoelectric scaffold (P) with calcium phosphate minerals (M). Damage scratches were introduced as band stripes. After re-immersing the sample for 7 days in SBF, the damaged regions were repopulated with minerals via piezoelectric mineralization, showing the self-healing capability.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Xu, A. W., Ma, Y., & Cölfen, H. (2007). Biomimetic mineralization. *Journal of Materials Chemistry*, 17(5), 415-449.

Meldrum, F. C., & Cölfen, H. (2008). Controlling mineral morphologies and structures in biological and synthetic systems. *Chemical Reviews*, 108(11), 4332-4432.

Lin, K. Wu, C., & Chang, J. (2014). Advances in synthesis of calcium phosphate crystals with controlled size and shape. *Acta Biomaterialia*, 10(10), 4071-4102.

Gupta, A. K. Naregalkar, R. R., Vaidya, V. D., & Gupta, M. (2007). Recent advances on surface engineering of magnetic iron oxide nanoparticles and their biomedical applications.

Alves, N. M., Leonor. I. B., Azevedo, H. S., Reis, R. L., & Mano, J. F. (2010). Designing biomaterials based on biomineralization of bone. *Journal of Materials Chemistry*, 20(15), 2911-2921.

Mann, S. (2001). Biomineralization: principles and concepts in bioinorganic materials chemistry (Vol. 5). Oxford University Press.

Kepa, K., Coleman, R., & Grondahl, L. (2015). In vitro mineralization of functional polymers. *Biosurface and Biotribology* 1(3), 214-227.

Stitz, N., Eiben, S., Atanasova, P., Domingo. N., Leineweber, A., Burghard, Z., & Bill, J. (2016). Piezoelectric Templates-New Views on Biomineralization and Biomimetics. *Scientific Reports*. 6.

Zhu, P., Masuda, Y., & Koumoto, K. (2004). The effect of surface charge on hydroxyapatite nucleation. *Biomaterials*, 25(17), 3915-3921

Mount, Andrew S., et al. "Deposition of nanocrystalline calcite on surfaces by a tissue and cellular biomineralization." U.S. Pat. No. 8,541,031. 24 Sep. 2013.
Sfeir, Charles, et al. "Method of inducing biomineralization method of inducing bone regeneration and methods related thereof." U.S. patent application Ser. No. 10/568,998.
Mount, Andrew S., et al. "Deposition of nanocrystalline calcite on surfaces by a tissue and cellular biomineralization." U.S. Pat. No. 9,371,451. 21 Jun. 2016.
McLeroy, Stacey L., et al. "Functionalization of Micro-And Nano Particles for Selective Attachment to Calcium Biomineral Surfaces." U.S. patent application Ser. No. 12/324,718.
Rosi, Nathaniel L., and Chun-Long Chen. "Templates for controlling synthesis of nanoparticles into discrete assemblies." U.S. Pat. No. 9,206,233. 8 Dec. 2015.
Silver, Frederick H., and David Christiansen. "Process for the mineralization of collagen fibers, product produced thereby and use thereof to repair bone." U.S. Pat. No. 5,532,217. 2 Jul. 1996.
Murphy, William L., et al. "Mineralization and biological modification of biomaterial surfaces." U.S. Pat. No. 6,767,928. 27 Jul. 2004.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method comprising:
    positioning a substrate comprising a piezoelectric material in a bone graft that is in direct contact with a liquid; and
    applying a mechanical stress to the substrate;
    generating a charge on a surface of the substrate in response to applying the mechanical stress; and
    depositing a material from the liquid on the surface in response to generating the charge,
    wherein depositing the material on the surface adjusts a modulus of the substrate in the bone graft.

2. The method of claim 1, wherein the mechanical stress is applied for a period of time of about 0.5 h to about 2 weeks.

3. The method of claim 1, wherein the mechanical stress is applied at a frequency of about 0.5 Hz to about 10 Hz.

4. The method of claim 1, wherein the mechanical stress is applied at a force amplitude of about 0 N to about 5 N.

5. The method of claim 1, wherein the substrate increases in stiffness in a region of maximum stress in response to applying the mechanical stress to the substrate.

6. The method of claim 1, wherein depositing the material on the surface optimizes the material distribution of the substrate with respect to the mechanical stress applied.

7. The method of claim 1, further comprising controlling a rate and an amount of the material deposited on the surface based on the mechanical stress applied to the substrate.

8. The method of claim 1, wherein the piezoelectric material comprises a plurality of fibers or a plurality of particles.

9. The method of claim 8, wherein the plurality of fibers or plurality of particles has an average diameter of about 100 nm to about 100 micrometers.

10. The method of claim 1, wherein the piezoelectric material has a piezoelectricity coefficient of at least about 1 pC/N to about 2,000 pC/N.

11. The method of claim 1, wherein the piezoelectric material is selected from the group consisting of polyvinylidene fluoride (PVDF), poly(vinylidene fluoride trifluoroethylene) (PVDF-TrFE), lead zirconate titanate (Pb$[Zr_xTi_{1-x}]O_3$ $0<x<1$), barium titanate ($BaTiO_3$), berlinite ($AlPO_4$), quartz ($SiO_2$), potassium sodium tartrate ($KNaC_4H_4O_6*4H_2O$), topaz $Al_2SiO_4(F,OH)_2$, gallium orthophosphate ($GaPO_4$), Langasite ($La_3Ga_5SiO_{14}$), lead titanate ($PbTiO_3$), potassium niobate ($KNbO_3$), lithium niobate ($LiNbO_3$), lithium tantalate ($LiTaO_3$), sodium tungstate ($Na_2WO_3$), $Ba_2NaNb_5O_5$, $Pb_2KNb_5O_{15}$, Poly($\gamma$-benzyl $\alpha$,L-glutamate) (PBLG), Poly-L-lactide (PLLA), sodium potassium niobate ((K, Na)$NbO_3$), bismuth ferrite ($BiFeO_3$), a piezoelectric composite, collagen, and a combination thereof.

12. The method of claim 1, wherein the piezoelectric material is not chemically modified.

13. The method of claim 1, wherein the liquid is a solution, a suspension, or a supersaturated solution.

14. The method of claim 1, wherein the liquid includes a plurality of ions comprising $Ca^{2+}$, $HPO_4^{-2}$, $HCO_3^-$, $CO_3^{2-}$, $Cu^{2+}$, or a combination thereof.

15. The method of claim 14, wherein the plurality of ions is present at a concentration of greater than 1 mM.

16. The method of claim 1, wherein the liquid is a biological fluid.

* * * * *